US008728755B2

(12) United States Patent
Rodgers (10) Patent No.: US 8,728,755 B2
(45) Date of Patent: May 20, 2014

(54) MEASUREMENT OF SEQUESTERED CARBON (75) Inventor: William Rodgers, Randwick (AU)

(73) Assignee: Ocean Nourishment Corporation Pty Limited, Allambie Heights NSW (AU)

(*) Notice: Subject to any disclaimer, the term of this patent is extended or adjusted under 35 U.S.C. 154(b) by 910 days.

(21) Appl. No.: 12/672,840

(22) PCT Filed: Aug. 8, 2008

(86) PCT No.: PCT/AU2008/001148
§ 371 (c)(1),
(2), (4) Date: May 20, 2011

(87) PCT Pub. No.: WO2009/021269
PCT Pub. Date: Feb. 19, 2009

(65) Prior Publication Data
US 2011/0212479 A1    Sep. 1, 2011

(30) Foreign Application Priority Data
Aug. 10, 2007   (AU) ................ 2007904330

(51) Int. Cl.
C12Q 1/02      (2006.01)
C01B 31/00    (2006.01)

(52) U.S. Cl.
USPC ........................ 435/29; 423/445 R (58) Field of Classification Search
USPC ........................ 435/29; 423/445 R
See application file for complete search history.

(56) References Cited

U.S. PATENT DOCUMENTS 6,200,530 B1   3/2001   Markels, Jr.

FOREIGN PATENT DOCUMENTS

| JP | 2003-134958 | 5/2003 |
| WO | 95/29583 | 11/1995 |
| WO | 96/20589 | 7/1996 |
| WO | WO 00/65902 | 11/2000 |
| WO | WO 2006/024070 | 3/2006 |
| WO | WO 2009/021269 | 2/2009 |

OTHER PUBLICATIONS

Adhiya, J and Chisolm, S. Is Ocean Fertilization a Good Carbon Sequestration Option?; MIT Laboratory for Energy and the Environment Reports (2001) downloaded from http://www.whoi.edu/fileserver.do?id=57723&pt=10&p=39435 on Nov. 8, 2012.*

Rios et al. Chemical Composition of Phytoplankton and Particulate Organic Matter in the Ria De Vigo (NW Spain); Scientia Marina, vol. 62, No. 3 (1998) pp. 257-271.*

(Continued)

Primary Examiner — Susan Hanley
Assistant Examiner — Paul Martin
(74) Attorney, Agent, or Firm — Fish & Richardson P.C.

(57) ABSTRACT

Disclosed herein are methods and systems for determining an amount of carbon dioxide that can be sequestered from the atmosphere by a portion of an ocean. The methods or systems involve the following steps (a) determining which chemical element or elements would, when added to a photic zone of the portion, cause growth of a phytoplankton population in the portion; (b) determining a quantity of the chemical element or elements to be added to the photic zone whereby substantially all of the element or substantially all of at least one of the elements added would be consumed by the additional phytoplankton grown: and (c) calculating the amount of carbon dioxide that can be sequestered from the atmosphere based on the determined quantity of the chemical element or elements that would be added to the portion.

8 Claims, 3 Drawing Sheets (56) References Cited

OTHER PUBLICATIONS

International Search Report dated Oct. 28, 2008 from PCT/AU2008/001148.

International Preliminary Report on Patentability dated Nov. 18, 2009 from PCT/AU2008/001148.

Extended EP Search Report mailed Jul. 17, 2013 in related European Application No. 07719111.2, 6 pgs.

* cited by examiner

MEASUREMENT OF SEQUESTERED CARBON

This application is the national stage of International Application Number PCT/AU2008/001148, filed on Aug. 8, 2008, which is based on and claims the benefit of the filing date of Australian Application No. 2007904330, filed on Aug. 10, 2007, all of which as filed are incorporated herein by reference in their entireties.

TECHNICAL FIELD

Disclosed are methods and systems for determining the amount of carbon dioxide that can be sequestered from the atmosphere by a portion of an ocean that has been nourished with nutrients.

BACKGROUND ART

The carbon dioxide concentration in the atmosphere has been rising, primarily as a result of fossil fuel burning. The United Nations Framework Convention on Climate Change indicates that there is a need to reduce the $CO_2$ content of the atmosphere for climate and food security reasons.

A natural process by which carbon dioxide in the atmosphere is converted into organic carbon is known. Atmospheric carbon dioxide can dissolve in the ocean and exist in a dissolved or ionic form. This "inorganic carbon" can be converted into "organic carbon" by being taken into the bodies of marine phytoplankton through the process of photosynthesis.

The phytoplankton produced by this conversion eventually perish through age or are eaten by other marine organisms. The resulting dead or excreted biomass then falls to lower levels in the ocean. In this regard, a phenomenon is known whereby organic carbon sinks from the surface ocean to the deep ocean (occurring over most of the ocean) and a compensatory flux of carbon from the deep ocean to the surface occurs by upwelling and diffusion.

Whilst some of the organic carbon material is promptly exported to the deeper ocean, some is converted back into inorganic material in the surface ocean. The recently converted inorganic material can be used by a next generation of phytoplankton to form a new standing stock of organic material. This cycling of carbon in and out of the organic state eventually leads to substantially all of the dissolved inorganic carbon initially converted to organic material being exported from the surface ocean to the deeper ocean.

A process by which photosynthesis in the ocean is caused to increase may assist in decreasing atmospheric carbon dioxide levels by increasing the conversion of inorganic carbon (i.e. dissolved carbon dioxide) to organic carbon (i.e. phytoplankton vegetable matter).

In this respect, the conversion of carbon dioxide dissolved at the surface of the ocean to organic carbon during the sunlit periods is often limited by the availability of specific nutrients, for example, the macronutrient nitrogen or the micronutrient iron. Accordingly, a process of nourishing the ocean can be used to increase the mass of carbon in transit in the deep ocean by providing nutrients that are in short supply to increase photosynthesis and thereby convert a greater amount of inorganic carbon (i.e. dissolved carbon dioxide) to organic carbon.

Methods are known that involve the addition of nutrients such as nitrogen or iron to a body of water in order to increase photosynthesis and cause more carbon dioxide from the atmosphere to dissolve in the ocean. When carbon stored in the deep ocean is supplied by the atmosphere, the process is termed carbon dioxide sequestration. Related sequestration methods in this respect are disclosed in U.S. Pat. No. 5,992, 089, and by Jones (1996) in "Enhanced carbon dioxide uptake by the world's ocean" (Energy Convers. & Mgmt, 37, 1049-1052) and Jones and Young (1997) "Engineering a large sustainable world fishery" (Environmental Conservation, 24, 99-104).

SUMMARY OF THE DISCLOSURE

In a first aspect, there is provided a method for determining an amount of carbon dioxide that can be sequestered from the atmosphere by a portion of an ocean. The method comprises the steps of:
(a) determining which chemical element or elements would, when added to a photic zone of the portion, cause growth of a phytoplankton population in the portion;
(b) determining a quantity of the chemical element or elements to be added to the photic zone whereby substantially all of the element or substantially all of at least one of the elements added would be consumed by the additional phytoplankton grown; and
(c) calculating the amount of carbon dioxide that can be sequestered from the atmosphere based on the determined quantity of the chemical element or elements that would be added to the portion.

The method described above may readily be used to quantify the amount of carbon dioxide that can be sequestered from the atmosphere by adding a known quantity of a nutrient containing a specific element or elements to the ocean.

In some embodiments, the amount of carbon dioxide that can be sequestered from the atmosphere may be calculated using the quantity of the chemical element or elements determined in step (b) and the Redfield ratio.

As will be appreciated, the exact ratio of chemical elements in phytoplankton may vary slightly from the Redfield Ratio in different regions of the oceans. Such embodiments can therefore only provide a "rough" indication of the quantity of carbon consumed by the additional phytoplankton grown and hence the amount of carbon dioxide that can be sequestered, which may be adequate for certain purposes.

However, some embodiments provide for a more precise determination of the amount of carbon dioxide that can be sequestered from the atmosphere. In such embodiments, the amount of carbon dioxide that can be sequestered from the atmosphere may be calculated using the quantity of the chemical element or elements determined in step (b) and a measured stoichiometric ratio of carbon and the one or more chemical elements in phytoplankton in the photic zone of the portion.

By using the actual stoichiometric ratio of elements present in phytoplankton in the portion (i.e. the "local Redfield Ratio") instead of the actual Redfield Ratio, the amount of carbon consumed by the additional phytoplankton grown, and hence the amount carbon dioxide that can be sequestered, can be more precisely calculated.

The chemical element or elements may, for example, be selected from the group consisting of nitrogen, phosphorous, silicon and iron.

The method of the first aspect may further comprise the step (d) of adding to the photic zone of the portion the quantity of the chemical element or elements required to cause growth of the phytoplankton population determined in step (b).

As phytoplankton growth is limited in some 80% of the ocean by the lack of the macronutrient nitrogen, nitrogen is typically the only chemical element added to the photic zone.

The nitrogen would typically be added in the foam of a nitrogen containing compound, for example, urea or ammonia.

In some embodiments, it may be necessary for step (c) to include a factor to compensate for inorganic carbon in the photic zone which is not replaced from the atmosphere, for example, in a situation where the nourished water is subducted away from contact with the atmosphere before the carbon consumed by the phytoplankton can be replaced from the atmosphere.

In some embodiments, it may be necessary for step (c) to include a factor to compensate for loss of chemical element or elements which are added to the photic zone but escape out of the photic zone before they can be consumed by the additional phytoplankton grown.

As one skilled in the art will appreciate, many countries have established carbon markets. Basically, industries which generate carbon dioxide (e.g. fossil fuel burning industries) are required (or in some countries given the option) to offset their carbon emissions by purchasing offset credits (also referred to herein as "carbon credits"). The method of the first aspect may be used to determine an amount of carbon credits from the amount of carbon dioxide calculated to be or actually sequestered.

In a second aspect, there is provided a method of producing carbon credits. The method comprises the steps of:
(a) determining which chemical element or elements would, when added to a photic zone of a portion of an ocean, cause growth of a phytoplankton population in the portion;
(b) determining a quantity of the chemical element or elements to be added to the photic zone whereby substantially all of the element or substantially all of at least one of the elements added would be consumed by the additional phytoplankton grown;
(c) adding to the photic zone of the portion the quantity of the chemical element or elements required to cause growth of the phytoplankton population determined in step (b);
(d) calculating the amount of carbon dioxide that will be sequestered from the atmosphere based on the determined quantity of the chemical element or elements that was added to the portion; and
(e) calculating the amount of carbon credits produced based on the amount of carbon dioxide that will be sequestered.

In a third aspect, there is provided a system for determining an amount of carbon dioxide that can be sequestered from the atmosphere by a portion of an ocean. The system comprises:
(a) using a water receptacle to obtain a sample of water from a photic zone of the portion;
(b) using an analyser to analyse the sample of water to determine which chemical element or elements would, when added to the photic zone, cause growth of a phytoplankton population in the portion, and to determine a quantity of the chemical element or elements whereby substantially all of the element or substantially all of at least one of the elements added would be consumed by the additional phytoplankton grown; and
(c) calculating the amount of carbon dioxide that can be sequestered from the atmosphere based on the determined quantity of the chemical element or elements that would be added to the portion.

In a fourth aspect, there is provided a system for producing carbon credits. The system comprises:
(a) using a water receptacle to obtain a sample of water from a photic zone of the portion;
(b) using an analyser to analyse the sample of water to determine which chemical element or elements would, when added to the photic zone, cause growth of a phytoplankton population in the portion, and to determine a quantity of the chemical element or elements whereby substantially all of the element or substantially all of at least one of the elements added would be consumed by the additional phytoplankton grown; and
(c) adding to the photic zone of the portion the quantity of the chemical element or elements required to cause growth of the phytoplankton population determined in step (b);
(d) calculating the amount of carbon dioxide that will be sequestered from the atmosphere based on the determined quantity of the chemical element or elements that was added to the portion; and
(e) calculating the amount of carbon credits produced based on the amount of carbon dioxide that will be sequestered.

In a fifth aspect, there is provided a carbon credit produced by embodiments of the method of the first aspect which comprise the step (d) described above, or the second aspect, or the system of the fourth aspect.

In a sixth aspect, there is provided a method for determining an amount of carbon dioxide sequestered from the atmosphere by a portion of an ocean. The method comprises the steps of adding to a photic zone of the portion a nutrient or nutrients that are consumable by phytoplankton to support photosynthesis by phytoplankton, and calculating the amount of carbon dioxide that will be sequestered based on the quantity of nutrient(s) consumed.

The method of the sixth aspect may be used to quantify the amount of carbon dioxide that can be sequestered from the atmosphere in situations where it is possible to calculate the quantity of a chemical element essential for growth of the phytoplankton population that will be consumed following addition of an excess amount of a nutrient.

Typically, the nutrient(s) are added to the photic zone in the local Redfield Ratio, although the actual Redfield Ratio may be used if desired. Typically, the nutrient is a nitrogen containing compound.

In a seventh aspect, there is provided a system, the system comprising:
a chemical element determiner for determining which chemical element or elements would, when added to a photic zone of a portion of an ocean, cause growth of a phytoplankton population in the portion;
a chemical element quantity determiner for determining a quantity of the chemical element or elements to be added to the photic zone whereby substantially all of the element or substantially all of at least one of the elements added would be consumed by the additional phytoplankton grown; and
a carbon dioxide sequestration calculator for calculating the amount of carbon dioxide that can be sequestered from the atmosphere based on the determined quantity of the chemical element or elements that would be added to the portion.

The system may comprise a computer, computer system, personal computer, computer server, a data farm, an embedded system or any other one or more suitable devices. The system may include a computer readable medium such as a hard drive, RAM, ROM, EPROM, EEPROM, flash memory or optical disk or other having a computer program.

In an eighth aspect, there is provided a computer program comprising instructions for controlling a computer to implement a method according to the first, second or sixth aspect, or the system of the third, fourth or seventh aspect.

In a ninth aspect, there is provided a computer readable medium providing a computer program in accordance with the eighth aspect.

BRIEF DESCRIPTION OF THE FIGURES

In order to achieve a better understanding of the methods and systems set forth in the summary, embodiments will now be described, by way of example only, with reference to the accompanying figures in which.

DETAILED DESCRIPTION OF SPECIFIC EMBODIMENTS

Specific embodiments of the methods and systems set forth in the summary will now be described.

The methods of the first and second aspects described above comprise the following steps:
(a) determining which chemical element or elements would, when added to a photic zone of a portion of an ocean, cause growth of a phytoplankton population in the portion; and
(b) determining a quantity of the chemical element or elements to be added to the photic zone whereby substantially all of the element or substantially all of at least one of the elements added would be consumed by the additional phytoplankton grown.

If a population of phytoplankton is not growing in a portion of an ocean, it is likely that the portion is deficient in a chemical element essential for growth of the phytoplankton population. In the step (a) set out above, a sample of water from the selected portion of the ocean can be analysed to determine which element or elements are deficient in the selected portion (i.e. which nutrient(s) is/are limiting the production of phytoplankton in that portion). This analysis would typically be made by analysing a water sample and/or a phytoplankton sample taken from the photic zone of the portion. Such analysis techniques are well known in the art and may involve using a water receptacle to obtain a sample of water from the photic zone of the portion and performing empirical experiments to establish which nutrient(s) are deficient in the water by measuring the chlorophyll response to the addition of various nutrients.

Often, it will be found that the portion is deficient in only one element (e.g. nitrogen, phosphorous or iron). However, it may sometimes be necessary to add a combination of elements in order to cause growth of the phytoplankton population (e.g. a combination of nutrients containing nitrogen and phosphorous).

In step (b), the quantity of the element(s) identified in step (a) to be added to the photic zone is calculated.

The quantity of the element(s) to be added must be carefully determined so that substantially all of the added element(s) will be consumed by the additional phytoplankton grown. This is necessary so that an accurate calculation of the amount of carbon dioxide that can be sequestered can be made based on the quantity of element(s) added.

In some embodiments, a specific quantity of the element(s) could be added in order to sequester a desired quantity of carbon dioxide (e.g. if a specific number of carbon credits are desired). Alternatively, the quantity of the element(s) to be added could be maximised such that both the added element and another element essential for the growth of the phytoplankton population were consumed by the additional phytoplankton.

The element may be added to the photic zone in any form which enabled the element to be used by the phytoplankton via photosynthesis. Typically, a nutrient (i.e. a compound or composition) containing the element would be used.

In embodiments of the sixth aspect, an excess amount of a nutrient or nutrients can be added to the portion. This would cause the phytoplankton population to grow until all of one (or more) of the chemical elements essential for growth of the phytoplankton population was consumed. The limiting chemical element may be present in the portion prior to addition of the nutrient, or may be in the nutrient itself. The amount of carbon dioxide that can be sequestered can then be calculated based on the quantity of the chemical element that will be consumed. Thus, in this aspect, the amount of carbon dioxide sequestered is not necessarily calculated based on the quantity of the chemical elements present in the added nutrient.

For example, many portions of the ocean contain sufficient macronutrients to sustain phytoplankton growth, but are deficient in the micronutrient iron and therefore phytoplankton growth is limited in these portions (these portions are referred to as "High nutrient, low chlorophyll zones"). However, if an excess of iron was added to the region, the phytoplankton population would grow until one of the macronutrients (e.g. nitrogen) was consumed. The amount of carbon dioxide sequestered could then be calculated based on the amount of nitrogen present in the photic zone of the portion of ocean when the iron nutrient was added. This can be readily determined from a sample of ocean water taken at the time of nourishment.

In some embodiments, it may only be necessary to roughly quantify the amount of carbon dioxide that could be sequestered. In such embodiments (referred to below as "the first embodiment"), the amount of carbon dioxide that can be sequestered from the atmosphere may be calculated using the quantity of the chemical element or elements determined in step (b) and the Redfield ratio.

The Redfield ratio can be used to describe the stoichiometric ratio of the elements C, N, Si, and P in phytoplankton living in the ocean. The Redfield ratio is typically about 106:16:15:1 (C:N:Si:P). Recent research has resulted in an expansion of the original ratio to include iron, where the ratio of C:N:Si:P:Fe is 106:16:15:1:0.001.

As a known quantity of the one or more elements has been added (at least one of which will substantially all be consumed by the additional phytoplankton grown) and it is assumed that the ratio of carbon to that element in phytoplankton grown will be in the Redfield Ratio, then the quantity of inorganic carbon that would be consumed by the phytoplankton following addition of the one or more elements can be calculated. Subject to the efficiency factors discussed below, substantially all of the inorganic carbon converted into organic carbon (i.e. phytoplankton) will be sequestered from the atmosphere.

As will be appreciated, the Redfield Ratio may vary slightly between different regions of the ocean (i.e. the ratio of C:N:Si:P in phytoplankton may not be exactly 106:16:15:1). The first embodiment may therefore only provide a "rough" indication of the amount of carbon dioxide sequestered, which may be adequate for certain purposes.

However, if it is necessary to more precisely determine the amount of carbon dioxide that can be sequestered from the atmosphere (e.g. if an exact number of carbon credits needs to be produced), in an alternate embodiment (referred to below as "the second embodiment"), the amount of carbon dioxide that can be sequestered from the atmosphere may be calculated using the quantity of the chemical element or elements determined in step (b) and a measured stoichiometric ratio of carbon and the one or more chemical elements in phytoplankton in the photic zone of the portion.

In the second embodiment, the Redfield ratio is not used, but the stoichiometric ratio of carbon to other element(s) in the phytoplankton in the portion is experimentally determined (i.e. a "local Redfield ratio" is determined). The stoichiometric ratio of carbon and the chemical element(s) in phytoplankton in the portion will indicate the relative proportions of elements required by the phytoplankton in that specific portion of the ocean. If the stoichiometric ratio of carbon to the selected chemical element(s) in phytoplankton taken from the portion is known, the amount of carbon consumed by the additional phytoplankton grown may be calculated more precisely than if the Redfield Ratio were used because the additional phytoplankton will have substantially the same stoichiometric ratio of elements to that of the measured phytoplankton.

In some embodiments, a verification process may also be undertaken, whereby a sample of water from the portion is taken and cultured with a relative quantity (i.e. in proportion to the volume of the sample) of the chemical element added to the portion to demonstrate complete uptake of the chemical element by the natural assemblages of phytoplankton present in the sample.

The chemical element(s) for addition to the photic zone in accordance with the methods and systems set forth in the Summary may be any element or combination of elements capable of causing the phytoplankton population to increase via photosynthesis.

Typically, the chemical element(s) is/are one or more of the elements included in the Redfield ratio, i.e. nitrogen, phosphorous, silicon and iron.

The chemical elements may be added to the photic zone of the portion in any convenient form. For example, when the chemical element is nitrogen, a nitrogen containing compound such as urea or ammonia can be added to the water in an appropriate stoichiometric amount.

It will be appreciated that depending on the nature of the surface currents where the chemical element(s) are added, the location of the increased phytoplankton population may not be the same as where the element(s) were added, but may be some distance down-current.

Whilst it will be necessary to actually physically sequester carbon dioxide in order to generate carbon credits, the amount of carbon dioxide sequesterable (and thus the amount of carbon credits which may be produced) may well need to be determined "on paper" before anything is added to the ocean. As such, not all of the methods or systems set forth in the Summary require a step in which an appropriate quantity of the chemical element or elements required to cause growth of the phytoplankton population is/are added to the portion.

For example, data may be available for specific portions of the ocean whereby the stoichiometric ratios of specific chemical elements in phytoplankton, as well as the limiting chemical element(s) in that portion, are known. As such, if a person wished to obtain a certain number of carbon credits, calculations could be made at any convenient location (e.g. at that person's workplace) based on the available data to determine the amount of what chemical element (e.g. the amount of urea if the portion is deficient in nitrogen) that would need to be added to sequester an amount of carbon dioxide sufficient to produce the desired number of carbon credits.

The appropriate amount of the limiting chemical element (e.g. nitrogen in the form of urea) could be added to the portion at a later stage, optionally along with additional amounts of the element if other people had also purchased carbon credits.

The appropriate quantity of the chemical element(s) (hereafter referred to simply as "nutrients") required to cause growth of the phytoplankton population may be added to the portion using any method.

For example, a nutrient (e.g. a compound or composition) containing an available source of the chemical element (e.g. superphosphate if the element is phosphorous, or urea or ammonia if the element is nitrogen) may be delivered to the photic zone of the portion via a pipeline which terminates in the portion (e.g. as disclosed in U.S. Pat. No. 5,992,089) or from a floating vessel such as a ship located above the portion.

In some embodiments, it may be necessary to include an efficiency factor to account for situations where not all of the nutrients added are immediately consumed by the additional phytoplankton grown, for example, in situations where not all of the inorganic carbon converted into organic carbon and exported from the photic zone is replaced from the atmosphere, and where not all of the carbon exported from the photic zone is sequestered for a significantly long period in the deep ocean.

In embodiments where the chemical element added to the photic zone is nitrogen (which is added in the form of a nitrogen containing compound such as urea or ammonia), an efficiency factor (Ef) taking into account the above situations may be calculated using the following formula:

$$Ef = A \times D \times S \times P1 \times P2 \times S \times Alkal$$

Where:
A is the air-sea transfer efficiency=0.99
D is the denitrification factor=0.95
S is the sequestration factor=0.99
P1 is greenhouse gas produced by the ocean=0.99
P2 is the greenhouse gas produced by chemical manufacture for ammonia=0.88
for urea=1.00
Alkal is the factor for change in ocean alkalinity for ammonia=0.87
for urea=1.02

The above factors can be determined by one skilled in the art for any particular region of the ocean and particular chemical element(s).

In some embodiments, it may be necessary to include an efficiency factor to compensate for loss of the chemical element or elements which are added to the photic zone, but which escape out of the photic zone and mixed layer (e.g. by processes such as subduction or mixed layer retreat) before they can be utilised to increase the phytoplankton population. Loss of such element(s) must be taken into account because they cannot be used in photosynthesis outside of the photic zone.

As those skilled in the art will appreciate, a significant amount of mixing of water in the upper levels of the ocean occurs daily as the result of wind surface currents. Provided its density is not too great, nutrients added to the mixed layer of the ocean will be recirculated throughout the mixed layer for a period of at least days.

Typically, the mixed layer extends from the surface of the ocean to a depth of about 50 meters. However, the mixed layer may extend to a depth of 100 meters or more. The actual depth of the mixed layer varies, and is dependent upon a number of factors including wind strength and the loss of heat due to the temperature difference between the oceanic surface waters and the lower atmosphere.

The photic zone extends to the depth that light penetrates into the ocean. It may be greater or less than the mixed layer depth, however, should the nutrients fall out of the photic zone, provided they remain in the mixed layer they will be recirculated back into the photic zone relatively quickly due to convective mixing throughout the mixed layer each night.

Typically, the portion is located such that carbon dioxide is sequestered from the atmosphere for a significant period of time (e.g. greater than 100 years). The deeper the dead phytoplankton and other derived organic matter sinks out of the photic zone, the longer the carbon is kept away from the surface area of the ocean. Thus, in at least preferred embodiments, the nutrient is delivered to the photic zone at a location where ocean currents will carry the nutrient and phytoplankton to a region of the ocean having a depth sufficient to allow dead said phytoplankton and organic material derived from the phytoplankton to fall from the mixed layer and enable carbon from the $CO_2$ to be sequestered from the atmosphere for a considerable time.

The portion may, for example, be located at the edge of a continental shelf, where the organic matter can sink to a depth of 1000 m or more.

A specific embodiment of the methods and systems set forth in the Summary will now be described, by way of example only.

As noted above, it is thought that phytoplankton growth is limited in up to 80% of the ocean by the lack of the macronutrient nitrogen. It is within the ability of a person skilled in the art to locate portions of the ocean deficient in nitrogen.

The amount of carbon dioxide sequestered from the atmosphere may be increased in such a portion (i.e. by causing an increase in the phytoplankton population) by adding a source of nitrogen (e.g. ammonia and/or urea) to the photic zone of the portion. Such activity is known as "Ocean Nourishment" (which is a trade mark of Earth, Ocean and Space Pty Ltd), which is the purposeful introduction of nutrients to the upper ocean for the purpose of storing carbon and enhancing the sustainable supply of marine protein.

The organic carbon produced by photosynthesis can be exported from the photic zone to the deep ocean and retained there for some time. This occurs either by subduction of surface waters or by sinking of particulate organic detritus out the upper ocean. It is believed that carbon dioxide may be sequestered from the atmosphere for at least 100 years, and possibly for up to 500 years or 1000 years, or even longer, depending on the location and ocean currents.

The urea or ammonia may be delivered to the photic zone by any manner, for example, from a ship or via a pipeline.

For example, if 1 tonne of urea was added to the surface ocean (and nitrogen was the limiting nutrient) the Redfield Ratio indicates that 2.65 tonnes of inorganic carbon will be taken from the surface ocean by additional phytoplankton grown.

If 2.65 tonnes of inorganic carbon was first added to the atmosphere (e.g. by burning fossil fuel), the atmosphere after 100% efficient Ocean Nourishment with 1 tonne of urea, would return to its same concentration of carbon (if the total alkalinity of the ocean did not change). This carbon uptake measure is known as the equivalent amount of carbon emission avoided.

A more specific example is described below.

One can consider a design to store about 5,000 tonnes per day of carbon ($5 \times 10^9$ g/d). With ample sunlight and nutrients the concentration of phytoplankton grows exponentially. Let us assume the concentration doubles each day. Then suddenly one nutrient is exhausted and growth stops. In this simple model half the phytoplankton mass is produced on the last day of growth. [ ... +2+4+8=16] Let us assume this growth is over a region 25 Km×20 Km. The uptake of carbon on the last day is $5 \times 10^9$ g/$2 \times 500$ Km$^2$=5 gCm$^{-2}$d$^{-1}$. For a 50 m deep photic (mixed layer) zone, 5 gm$^{-2}$d$^{-1}$ of carbon is 100 mgCm$^{-3}$d$^{-1}$ and needs 100/7 mgNm$^{-3}$, divided by the molecular weight (14)=1 mmoleNm$^{-3}$d$^{-1}$ or 1 μmoleL$^{-1}$Nd$^{-1}$. The total conversion of inorganic to organic carbon therefore is 10 gCm$^{-2}$ and N required is 2 μmolar (μM). The last figure comes from assuming the Redfield ratio of the constituents in phytoplankton.

In some embodiments, it may be advantageous to provide for all the nutrients (except carbon) used to produce phytoplankton via photosynthesis (e.g. in the Redfield Ratio). Then a portion of the ocean, subjected to Ocean Nourishment would, after the export of all new primary production (i.e. all additional nutrients added), return to much the same state as it was before Ocean Nourishment.

As noted above, in some aspects there are provided methods and systems for producing carbon credits, and carbon credits produced using such methods and systems.

Many countries and other entities have established carbon markets. Industries which generate carbon dioxide (e.g. fossil fuel burning industries) are required, or is some countries given the option, to offset their carbon emissions by purchasing offset credits. Such credits can, for example, be obtained by planting trees or more relevantly by bio-sequestration of carbon in the oceans through Ocean Nourishment. A calculation of the amount of carbon dioxide sequested can be used to determine the quantity of carbon offsets issued.

In this case, it is advantageous to have a system that can calculate the amount of carbon dioxide sequested through Ocean Nourishment. Such a system can also be used to optimise an Ocean Nourishment operation before its undertaking, and also be used to calculate the net benefit. Such a system can be used to determine the economics of an Ocean Nourishment operation, or used by financial backers of or other interested parties investing in an Ocean Nourishment project.

Figure 1:
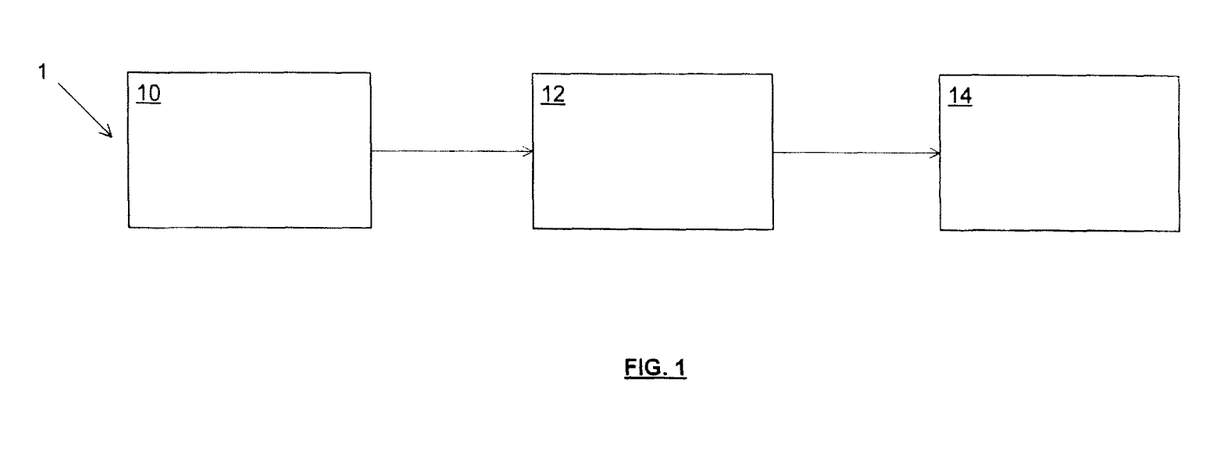
FIG. 1 shows a block diagram of one embodiment of a system in accordance with one aspect.

A block diagram of one embodiment of such a system is shown in FIG. 1 and generally indicated by the numeral 1. The system 1 comprises communicating components 10, 12 and 14. The system 1 has a chemical element determiner 10 for determining which chemical element or elements would, when added to a photic zone of a portion of an ocean, cause growth of a phytoplankton population in the portion. The chemical element determiner 10 may, for example, receive test results indicating the elemental composition of a water sample taken from the area that is intended to be nourished, and from this determine any elemental imbalances or deficiencies that could be corrected to promote growth of the phytoplankton population. Information generated by 10 is passed to a chemical element quantity determiner 12 for determining a quantity of the chemical element or elements to be added to the photic zone whereby substantially all of the element or substantially all of at least one of the elements added would be consumed by the additional phytoplankton grown. The information generated by 12 is passed to a carbon dioxide sequestration calculator 14 for calculating the amount of carbon dioxide that can be sequestered from the atmosphere based on the determined quantity of the chemical element or elements that would be added to the portion. The calculated information on the amount of carbon dioxide sequested can then be used to determine the number of carbon offset credits issued. For example, if 10 MT of carbon dioxide was calculated as being sequestered then 10 million offsets each capable of being spent against 1 tonne on carbon dioxide emitted may be issued.

Figure 2:
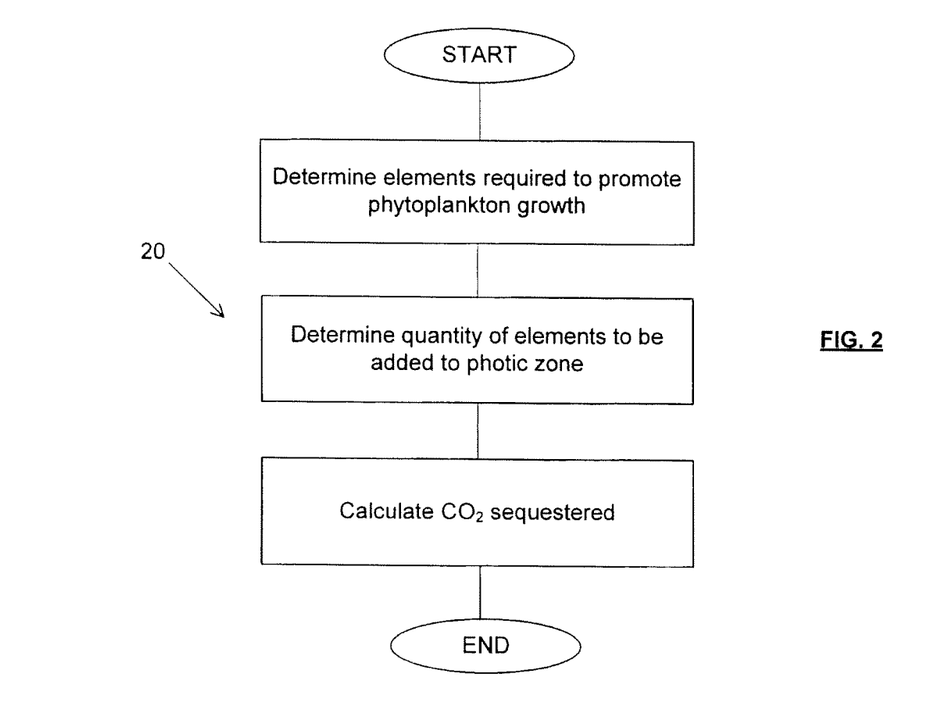
FIG. 2 shows a flow diagram of one embodiment of a method in accordance with one aspect.
Figure 3:
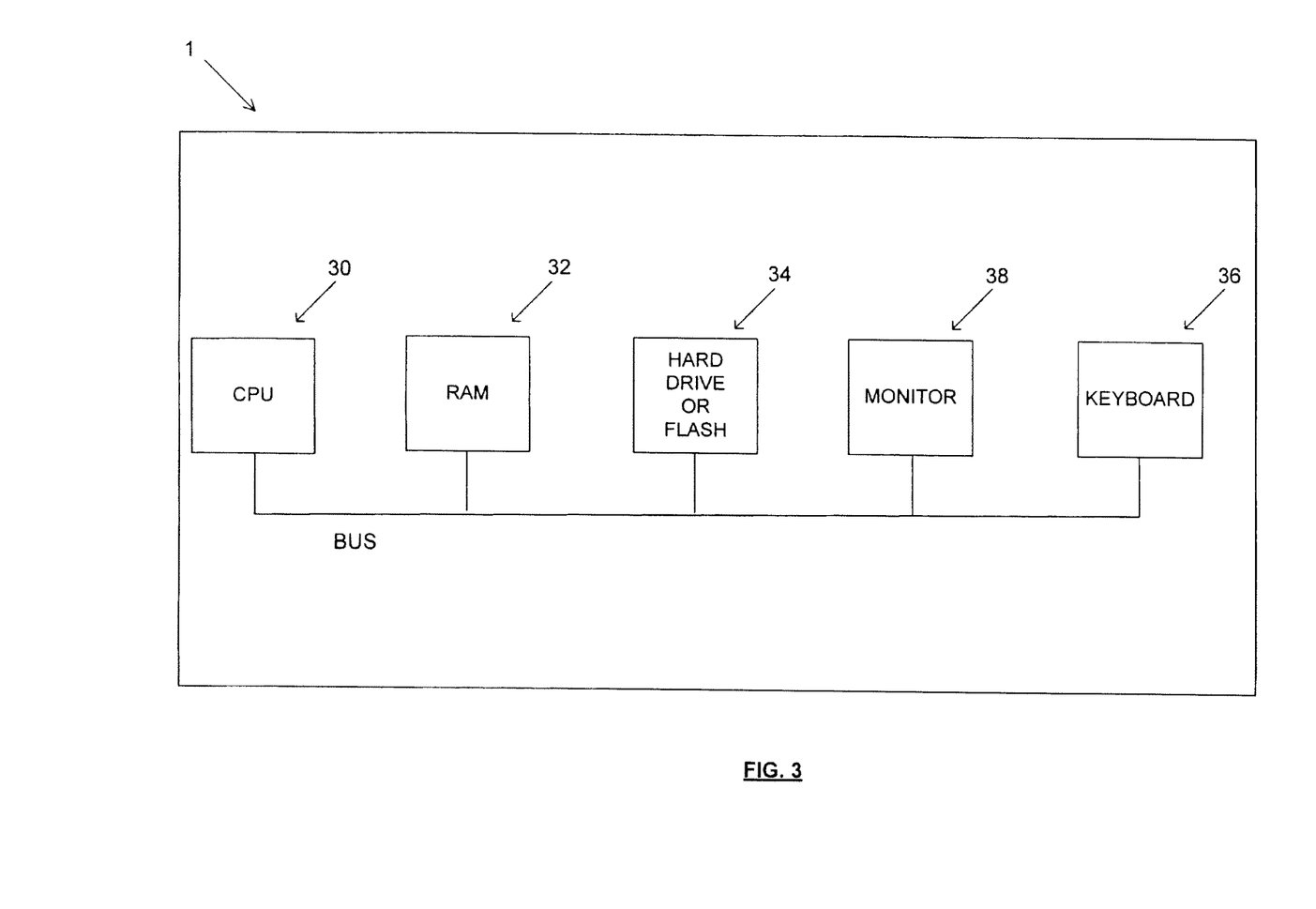
FIG. 3 shows a block diagram of the architecture of one embodiment of the system of FIG. 1.

The system 1 may comprise a computer, computer system, personal computer, computer server, a data farm, an embedded system or any other one or more suitable devices. The system may include a computer readable medium such as a hard drive, RAM, ROM, EPROM, EEPROM, flash memory or optical disk or other having a computer program. The computer readable medium may store a computer program comprising instructions for controlling the system 1 to implement a method such as the example method shown in FIG. 2 and generally indicated by the numeral 20. As shown in FIG. 3, the computer program may run on a central processor 30 of the system 1 connected to the memory 32 and 34 over a bus, and also connected to input and output devices such as keyboards 36, monitors 38, printers, and also network interfaces as required.

Of course the system 1 and method 20 can be modified to achieve any variation or combination of features disclosed herein.

It is envisaged that the methods and systems disclosed herein, which could be used to sequester carbon dioxide from the atmosphere for a significant period of time, could be a very cost effective way to offset an industry's carbon emissions.

A current method to sequester carbon involves capturing carbon dioxide from a stream of gas, compressing the captured gas and then injecting it into porous rocks under the ground. As will be appreciated, this process is likely to be more energy intensive that the methods and systems described above.

It will be appreciated by those skilled in the art that the methods and systems set forth in the Summary are not intended to be limited by the specific embodiments described above.

A reference herein to a prior art document is not an admission that the document forms part of the common general knowledge in the art in Australia or in any other country.

In the claims which follow and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments.

The invention claimed is:

1. A method for determining an amount of carbon dioxide that can be sequestered from the atmosphere by a portion of an ocean, the method comprising:
    (a) obtaining a sample comprising water and phytoplankton from a photic zone of a portion of an ocean;
    (b) analysing the water and the phytoplankton in the sample to determine the stoichiometric ratio of carbon to other chemical elements in the water and in the phytoplankton;
    (c) determining which one or more of the other chemical elements would, when added to the photic zone of the portion, cause growth of a phytoplankton population in the portion;
    (d) calculating a quantity of the one or more chemical elements determined in step (c), whereby substantially all of the element or substantially all of at least one of the elements added to the photic zone of the portion would be consumed by the additional phytoplankton grown; and
    (e) calculating the amount of carbon dioxide that can be sequestered from the atmosphere using the quantity of the chemical element or elements determined in step (d) and the stoichiometric ratio of carbon to other chemical elements in phytoplankton determined in step (b).

2. The method of claim 1, wherein the other chemical elements are nitrogen, phosphorous, silicon and iron.

3. The method of claim 1, wherein step (e) includes a factor to compensate for inorganic carbon in the photic zone which is not replaced from the atmosphere.

4. The method of claim 1, wherein step (e) includes a factor to compensate for loss of chemical element or elements which are added to the photic zone but escape out of the photic zone before they can be consumed by the additional phytoplankton grown.

5. A method for determining an amount of carbon dioxide that can be sequestered from the atmosphere by a portion of an ocean and adding chemical elements to increase phytoplankton growth, the method comprising:
    (a) obtaining a sample comprising water and phytoplankton from a photic zone of a portion of an ocean;
    (b) analysing the water and the phytoplankton in the sample to determine the stoichiometric ratio of carbon to other chemical elements in the water and in the phytoplankton;
    (c) determining which one or more of the other chemical elements would, when added to the photic zone of the portion, cause growth of a phytoplankton population in the portion;
    (d) calculating a quantity of the one or more chemical elements determined in step (c), whereby substantially all of the element or substantially all of at least one of the elements added to the photic zone of the portion would be consumed by the additional phytoplankton grown;
    (e) calculating the amount of carbon dioxide that can be sequestered from the atmosphere using the quantity of the chemical element or elements determined in step (d) and the stoichiometric ratio of carbon to other chemical elements in phytoplankton determined in step (b); and
    (f) adding to the photic zone of the portion the quantity of the chemical element or elements calculated in step (d) to increase phytoplankton growth.

6. The method of claim 5, wherein nitrogen is the only of the other chemical elements added to the photic zone and the nitrogen is added in the form of a nitrogen containing compound.

7. The method of claim 6, wherein the nitrogen containing compound is urea or ammonia.

8. A method for determining an amount of carbon credits from an amount of carbon dioxide that can be sequestered from the atmosphere by a portion of an ocean, the method comprising:
    (a) obtaining a sample comprising water and phytoplankton from a photic zone of a portion of an ocean;
    (b) analysing the water and the phytoplankton in the sample to determine the stoichiometric ratio of carbon to other chemical elements in the water and in the phytoplankton;
    (c) determining which one or more of the other chemical elements would, when added to the photic zone of the portion, cause growth of a phytoplankton population in the portion;
    (d) calculating a quantity of the one or more chemical elements determined in step (c), whereby substantially all of the element or substantially all of at least one of the elements added to the photic zone of the portion would be consumed by the additional phytoplankton grown;

(e) calculating the amount of carbon dioxide that can be sequestered from the atmosphere using the quantity of the chemical element or elements determined in step (d) and the stoichiometric ratio of carbon to other chemical elements in phytoplankton determined in step (b); and
(f) determining an amount of carbon credits from the amount of carbon dioxide calculated to be or actually sequestered.

* * * * *